(12) United States Patent
Diedrich et al.

(10) Patent No.: US 7,544,233 B2
(45) Date of Patent: Jun. 9, 2009

(54) GAS CHROMATOGRAPH WITH A MASS SPECTROMETER SITUATED DOWN THEREFROM, AND METHOD FOR PERFORMING THE GAS CHROMATOGRAPHIC/MASS SPECTROMETRIC ANALYSIS OF A SUBSTANCE MIXTURE

(75) Inventors: Frank Diedrich, Karlsruhe (DE); Friedhelm Müller, Linkenheim-Hochstetten (DE)

(73) Assignee: Siemens Aktiengesellsachaft, Munich (DE)

(*) Notice: Subject to any disclaimer, the term of this patent is extended or adjusted under 35 U.S.C. 154(b) by 298 days.

(21) Appl. No.: 10/554,162

(22) PCT Filed: Apr. 28, 2004

(86) PCT No.: PCT/EP2004/004483

§ 371 (c)(1),
(2), (4) Date: Aug. 7, 2006

(87) PCT Pub. No.: WO2004/097398

PCT Pub. Date: Nov. 11, 2004

(65) Prior Publication Data
US 2006/0272506 A1 Dec. 7, 2006

(30) Foreign Application Priority Data
Apr. 28, 2003 (DE) .............................. 103 19 130

(51) Int. Cl.
*B01D 53/02* (2006.01)
(52) U.S. Cl. .............................. 95/82; 96/102; 96/106; 73/23.36; 73/23.4

(58) Field of Classification Search .................... 95/82; 96/101, 102, 106; 73/23.35, 23.36, 23.37, 73/23.4, 23.42
See application file for complete search history.

(56) References Cited

U.S. PATENT DOCUMENTS

| 3,405,549 A | 10/1968 | Finley |
| 3,581,465 A * | 6/1971 | Haruki et al. ................... 95/87 |
| 4,123,236 A | 10/1978 | Hirschfeld et al. |

(Continued)

FOREIGN PATENT DOCUMENTS

| DE | 1 598 568 | 1/1971 |
| DE | 101 05 728 A1 | 9/2002 |

OTHER PUBLICATIONS

D.B. Kassel, B.D. Musselman, and J.A. Smith, "Primary Structure Determination of Peptides and Enzymatically Digested Proteins Using Capillary Liquid Chromatography/Mass Spectrometry and Rapid Linked-Scan Techniques", American Clerical Society, Analytical Chemistry, Jun. 1, 1991, pp. 1091-1097, vol. 63, No. 11, Massachusetts, USA.

*Primary Examiner*—Duane Smith
*Assistant Examiner*—Robert A Clemente

(57) ABSTRACT

The aim of the invention is to optimize the analysis of substances separated by gas chromatography with a gas chromatograph, comprising a separating device and a mass spectrometer situated down there from. To this end, a detector that detects the separated substances in a nondestructive manner is placed in-line between the output of the separating device and a controllable inlet valve of the mass spectrometer. An evaluating device situated down from the detector evaluates the detector signals and, based on the evaluation, controls the inlet valve for introducing predeterminable substances into the mass spectrometer.

4 Claims, 1 Drawing Sheet

U.S. PATENT DOCUMENTS

| | | | | |
|---|---|---|---|---|
| 5,281,397 A | * | 1/1994 | Ligon et al. | 422/89 |
| 5,686,655 A | * | 11/1997 | Itoi | 73/23.37 |
| 5,811,059 A | | 9/1998 | Genovese et al. | |
| 6,351,983 B1 | * | 3/2002 | Haas et al. | 73/23.37 |
| 6,460,401 B1 | * | 10/2002 | Hoshino et al. | 73/23.35 |
| 6,706,534 B2 | * | 3/2004 | Sacks et al. | 436/161 |
| 6,706,535 B2 | * | 3/2004 | Sacks et al. | 436/161 |
| 6,952,946 B2 | * | 10/2005 | Mueller | 73/23.4 |
| 7,148,475 B2 | * | 12/2006 | Cozic et al. | 250/288 |
| 7,269,994 B2 | * | 9/2007 | Umemura | 73/23.37 |

* cited by examiner

GAS CHROMATOGRAPH WITH A MASS SPECTROMETER SITUATED DOWN THEREFROM, AND METHOD FOR PERFORMING THE GAS CHROMATOGRAPHIC/MASS SPECTROMETRIC ANALYSIS OF A SUBSTANCE MIXTURE

CROSS REFERENCE TO RELATED APPLICATIONS

This application is the US National Stage of International Application No. PCT/EP2004/004483, filed Apr. 28, 2004 and claims the benefit thereof. The International Application claims the benefits of German application No. 10319130.5, filed Apr. 28, 2003, both applications are incorporated by reference herein in their entirety.

FIELD OF INVENTION

The invention relates to a gas chromatograph with downstream mass spectrometer and a method for gas chromatographic mass spectrometric analysis of a substance mixture.

SUMMARY OF THE INVENTION

For gas chromatographic analysis of a substance mixture this mixture is directed together with a carrier gas through a chromatographic separation device in which the substances of the substance mixture are separated as a result of their different retention times and thus appear one after the other at the output of the separation device. Different detectors, such as heat conductivity detectors or flame ionization detectors for example, are available for the detection of the separated materials. The use of a mass spectrometer as detector also makes it possible, in addition to detecting the chromatographically separated materials, to differentiate between materials with the same retention times but different masses. Since the mass spectrometric analysis of materials is undertaken in a vacuum, the presence of the carrier gas which comes out of the gas chromatograph together with the separated materials is undesired. The mass spectrometer is thus connected via a controllable inlet valve to the output of the separation device, said inlet valve only being opened on demand, that is on arrival of the separated materials, with the carrier gas being removed as well (DE 1598568). Although it is possible to detect in the removed carrier gas the arrival of the separated substance mixture and to open the inlet valve as a function of this event, a part of the separated material, namely that material removed at the start with the carrier gas, is lost to mass spectrometric analysis in this case. The control of the feeding of separated materials to the mass spectrometer can thus only be undertaken in a relatively crude manner by adhering to safety times, so that a not insignificant amount of carrier gas gets into the mass spectrometer and a correspondingly high pump power is required to generate the necessary vacuum.

The underlying object of the invention is thus to optimize the mass spectrometric analysis of gas chromatographically separated materials.

In accordance with the invention the object is achieved by a gas chromatograph with a downstream mass spectrometer which is connected via a controllable inlet valve to the output of a separation device of the gas chromatograph separating the materials passing through it, with a detector detecting the separated materials in a non-destructive manner being arranged between the output of the separation device and the inlet valve in-line and an evaluation device being arranged downstream from the detector which evaluates the detector signals generated by the detector and, depending on these signals, controls the inlet valve to introduce predetermined materials into the mass spectrometer.

The object is further achieved by a method for gas chromatographic mass spectrometric analysis of a substance mixture, which, for separation of the materials contained in it, is directed by means of a carrier gas through a separation device, at the output of which the separated materials arriving there are introduced for quantitative determination via a controllable inlet valve into a mass spectrometer, with the separated materials being detected by a detector arranged in-line between the output of the separation device and the inlet valve, and depending on the detection, the inlet valve is controlled for introduction of predetermined materials into the mass spectrometer.

The separated materials appearing at the output of the separation device are detected in-line and non-destructively, with only those materials being forwarded to the mass spectrometer which have been selected for a further mass spectrometric analysis. As a result of the speed of the carrier gas stream the time taken by the materials to pass from the detector to the inlet valve of the mass spectrometer is known, so that the materials can be transferred very selectively to the mass spectrometer and thus the amount of carrier gas entering the mass spectrometer is minimal. The pump power for creation of the vacuum in the mass spectrometer can thus be correspondingly small, so that very small pumps, e.g. ion getter pumps, can be employed. This produces benefits as regards costs, service life, maintenance requirements and power consumption. Further the scope of measurement signal evaluation in the mass spectrometer is restricted just to the materials fed selectively to it, so that its electronics and software can be designed to be cheaper and more powerful (fast).

Materials which are not selected for mass spectrometric analysis can if necessary still be analyzed by the in-line detector and the downstream evaluation unit.

The only detectors employed are those which do not destroy the substance mixture, i.e. a suitable heat conductivity detector, optical detector or detector operating with surface acoustic waves for example. In order not to adversely affect the separation performance of the separation device, the measurement path through which the substance mixture flows in this case is preferably embodied by the detector such that its cross sectional dimensions correspond at least approximately to the cross sectional dimensions of the separation device.

In accordance with a preferred embodiment of the inventive gas chromatograph mass spectrometer the detector consists of a heat conductivity detector with heat resistors arranged in a bridge circuit, of which two heat resistors lying diagonally opposite one another in the two different halves of the bridge circuit are arranged in the measurement path; the two other heat resistors then lie for example in a reference path through which the carrier gas flows.

For further explanation of the invention reference is made below to the Figures of the drawing.

DETAILED DESCRIPTION OF INVENTION

Figure 1:
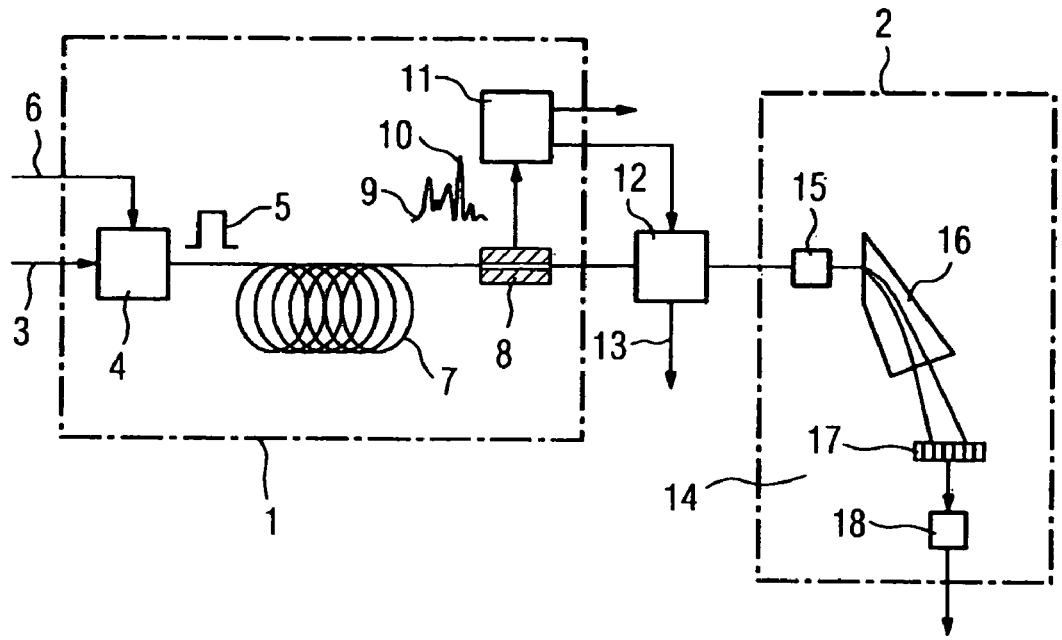
FIG. 1 shows an exemplary embodiment of the inventive gas chromatograph mass spectrometer.

FIG. 1 shows a gas chromatograph 1 with a downstream mass spectrometer 2 for analysis of a substance mixture (sample) 3, which is fed, after being taken out of a technical process and prepared, to a dosing device 4. The dosing device 4 is used to feed at a predetermined point in time a predetermined dosing amount of the sample 3 in the form of a short and precisely limited sample drop 5 into a carrier gas stream 6 and feed it to a separation device 7 in the form of a separation column or separation column circuit. The separation device 7 separates the materials contained in the sample drop 5 in accordance with their retention periods, so that the materials appear at the output of the separation device 7 in turn.

A detector 8 for detecting the separated materials is arranged at the output of the separation device 7. The detector 8 delivers a detector signal 9 which contains a peak 10 for each separated material, the surface of said peak being proportional to the amount of material. In an evaluation unit 11 arranged downstream from the detector 8, the arrival of selected materials is determined on the basis of their peaks 10 and, depending on this event and on the carrier gas speed, an inlet valve 12 between the detector 8 and the mass spectrometer 2 is controlled such that this valve only introduces the selected materials into the mass spectrometer 2 and removes the other materials as well as the carrier gas via an outlet 13.

The selected materials arriving in the vacuum 14 of the mass spectrometer 2 are ionized in a zone source 15, then separated in a mass filter 16 in accordance with their mass/charge ratio and finally verified by means of a detector array 17 with downstream evaluation device 18.

Figure 2:
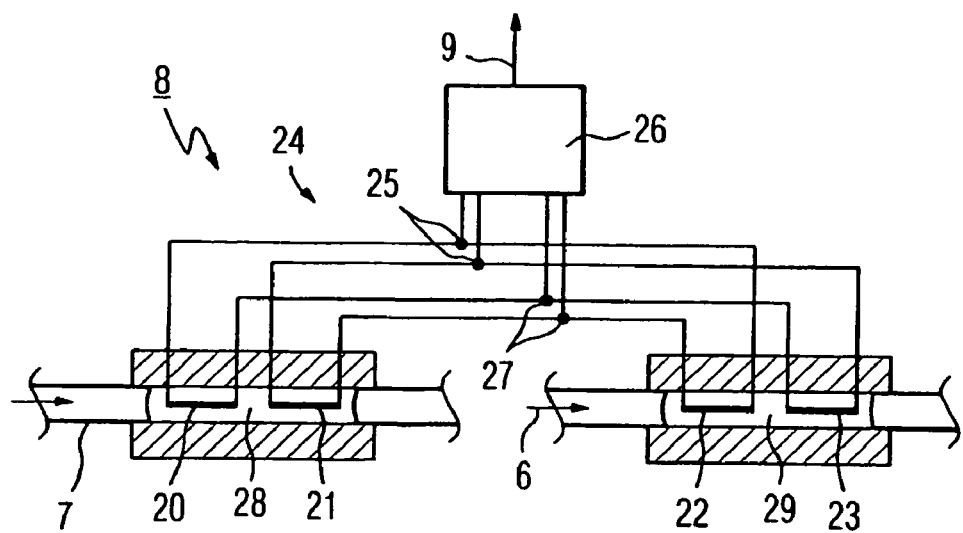
FIG. 2 shows an exemplary embodiment for the detector.

FIG. 2 shows an example of the in-line detector 8 which is embodied in this diagram as a heat conductivity detector. The detector 8 features wire-wound heat resistors 20, 21, 22, 23 arranged in a bridge circuit 24, with the bridge circuit 24 being fed at two opposite circuit points 25 from a detector circuit 26 with a current, and the voltage of the detector circuit 26 occurring between the two other opposing circuit points 27 being recorded for generation of the detector signal. The heat resistors 20 and 21 lying diagonally opposite one another in the bridge circuit 24 are arranged between the separation device 7 and the inlet valve 12 in a measurement path 28 of the detector 8, while the two remaining heat resistors 22 and 23 are arranged in a reference path 29 through which the carrier gas 6 flows. The measurement path 28 is embodied such that its internal cross-sectional dimensions correspond to those of the connected separation device 7, so that the separated substance mixture flowing through it is not destroyed. The heat resistors 20, 21, 22, 23 and the inner walls of the paths 28, 29 are made of materials which behave in an inert way in relation to the substance mixture to be analyzed or to the support gas 6, for example gold or silicon dioxide (quartz), so that a change in the substance mixture as a result of chemical reactions is excluded.

The invention claimed is:

1. A method for gas chromatographic analysis of a substance mixture, the method comprising:
   directing the substance mixture for separation of the materials contained within it by means of a carrier gas through a separation device at the output of which the materials spatially separated in groups are introduced for quantitative determination via a controllable inlet valve into a mass spectrometer, there being an alternate outlet for release of the carrier gas; and
   detecting the separated materials by a detector arranged in-line between the output of the separation device and the inlet valve and, as a function of the detection, the inlet valve being controlled for introduction of all detected materials into the mass spectrometer, the inlet valve and alternate outlet otherwise controlled to admit all carrier gas into the alternate outlet instead of the mass spectrometer.

2. The method of claim 1 wherein the step of detecting the separated materials by the detector includes providing a detector which comprises a measurement path through which the substance mixture passes of which cross-sectional dimensions at least approximately correspond to cross-sectional dimensions of the separation device.

3. The method of claim 1 wherein the step of detecting the separated materials by the detector includes providing a heat conductivity detector.

4. The method of claim 3 wherein the step of providing the heat conductivity detector comprises providing heat resistors arranged in a bridge circuit, wherein two heat resistors lie diagonally opposite one another in two different halves of the bridge circuit in the measurement path.

* * * * *